(12) United States Patent
Moloney et al.

(10) Patent No.: US 6,288,304 B1
(45) Date of Patent: *Sep. 11, 2001

(54) EXPRESSION OF SOMATOTROPIN IN PLANT SEEDS

(75) Inventors: Maurice M. Moloney; Hamid R. Habibi, both of Calgary (CA)

(73) Assignee: SemBioSys Genetics Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/210,843

(22) Filed: Dec. 18, 1998

Related U.S. Application Data

(63) Continuation-in-part of application No. 08/846,021, filed on Apr. 25, 1997, now Pat. No. 5,948,682, which is a continuation-in-part of application No. 08/366,783, filed on Dec. 30, 1994, now Pat. No. 5,650,554, which is a continuation-in-part of application No. 08/142,418, filed on Nov. 16, 1993, now abandoned, which is a continuation-in-part of application No. 07/659,835, filed on Feb. 22, 1991, now abandoned.

(51) Int. Cl.⁷ ............................ C12N 15/18; C12N 15/29; C12N 15/62; C12N 15/82; A01H 5/00
(52) U.S. Cl. ...................... 800/288; 800/278; 800/287; 800/306; 800/310; 800/312; 800/313; 800/314; 800/320.1; 800/322; 435/69.4; 435/69.7; 435/468; 536/23.4; 536/23.51; 536/23.6
(58) Field of Search .................................. 435/69.7, 69.4, 435/468; 536/23.6, 23.51, 23.4; 800/288, 278, 306, 310, 312, 313, 314, 322, 320.1, 287

(56) References Cited

U.S. PATENT DOCUMENTS 5,650,554 7/1997 Moloney et al. ..................... 800/205

FOREIGN PATENT DOCUMENTS 0193259 9/1986 (EP) .

OTHER PUBLICATIONS

Karen et al. Gene 77:309–315, 1989.*

Radke et al., "Transformation of *Brassica napus* L. using *Agrobacterium tumefaciens*: Developmentally Regulated Expression of a Reintroduced Napin Gene", Theor. Appln. Genet. (1988) 75:685–694.

Taylor et al., Storage–protein Regulation and Lipid Accumulation in Microspore embryos of *Brassica napus* L. , Planta (1990) 181:18–26.

Sijmons et al., "Production of Correctly Processed Human Serum Albumin in Transgenic Plants" Bio/Technology (1990) 8:217–221.

Huang, "Lipid Bodies" Modern Methods Plant Analysis (1985) 1:145–151.

Misra and Gedamu, "Heavy Metal Tolerant Transgenic *Brassica napus* L. and *Nicotiana tabacum* L. Plants" Theor. Appl. Genet. (1989) 78:161–168.

Hatzopoulos et al., "Interaction of Nuclear Factors with Upstream Sequences of Lipid Body Membrane Protein Gene from Carrot" The Plant Cell (1990) 2:457–467.

Lee et al., "Maize Oleosin is Correctly Targeted to Seed Oil Bodies in *Brassica napus* Transformed with the Maize Oleosin Gene" PNAS USA (1991) 88:6181–6185.

Vance and Huang, "Expression of Lipid Body Protein Gene during Maize Seed Development" J. Biol. Chem. (1988) 263:1476–1481.

Vance and Huang, "The Major Protein from Lipid Bodies of Maize" J. Biol. Chem. (1987) 262:11275–11279.

Qu and Huang, "Oleosin KD 18 on the Surface of Oil Bodies in Maize"J. Biol. Chem (1990) 265:2238–2243.

Sengupta–Gopalan et al., "Developmentally Regulated Expression of the Bean Beta–phaseolin Gene in Tobacco Seed" PNAS USA (1985) 82:3320–3324.

Fraley et al., "Expression of Bacterial Genes in Plant Cells" PNAS USA (1983) 80:4803–4807.

Vanderkerckhove et al., "Enkephalins Produced in transgenic Plants using Modified 2S Seed Storage Proteins" BIO/Technology (1989) 7:929–932.

Murphy et al., "Synthesis of the Major Oil–body Membrane Protein in Developing Rapeseed (*Brassica napus*) Embryos" Biochem J. (1989) 258:285–293.

Qu et al., "Characteristics and Biosynthesis of Membrane Proteins of Lipid Bodies in the Scutella of Maize (*Zea mays* L.)" Biochem. J. (1986) 235:57–65.

Josefsson et al., "Structure of a Gene Encoding the 1.7 S Storage Protein Napin, from *Brassica napus*" J. Biol. Chem (1987) 262:12196–12201.

Scofield and Crouch, "Nucleotide Sequence of A Member of the Napin Storage Protein Family From *Brassica napus*" J. Biol. Chem. (1987) 262:12202–12208.

Fujikawa et al., "Bovine Factor X1 (Stuart Factor), Mechanism of Activation by a Protein from Russell's Viper Venom" Biochemistry (1972) 11:4892–4899.

Nagai et al., "Oxygen Binding Properties of Human Mutant Hemoglobins Synthesized in *Escherichia coli*" PNAS USA (1985) 82:7252–7255.

(List continued on next page.)

Primary Examiner—David T. Fox
(74) Attorney, Agent, or Firm—Bereskin & Parr; Micheline Gravelle

(57) ABSTRACT

The present invention provides a method of preparing somatotropins in plants and transgenic plant seeds containing somatotropins. The method provides an economical way to produce somatotropins.

19 Claims, 4 Drawing Sheets

OTHER PUBLICATIONS

Scholtissek and Grosse, "A Plasmid Vector System for the Expression of a Triprotein Consisting of Beta–galactosidase, a Collagenase Recognition Site and a Foreign Gene Product" Gene (1988) 62:55–64.

Bevan, "Binary Agrobacterium Vectors for Plant Transformation" Nucl. Acids. Res. (1984) 12:8711–8721.

Murphy et al., "A class of Amphipathic Proteins Associated with Lipid Storage Bodies in Plants" Biochem. Biophys. Acta (1991) 1088:86–94.

Antoni et al., "A Short Synthetic Peptide Fragment of Human Interleukin 1 with Immunostimulatory But not Inflammatory Activity" J. Immunol. (1986) 137:3201–3204.

An et al., "New Cloning Vehicles for Transformation of Higher Plants" Embo J. (1985) 4:277–284.

Hood et al., "The Hypervirulence of *Agrobacterium tumefaciens* A281 is encoded in a Region of pTiBo542 outside of T–DNA" J. Bacteriol. (1986) 168:1291–1301.

Holbrook et al., "Oilbody Proteins in Microspore–derived Embryos of *Brassica napus*" Plant Physiol. (1991) 97:1051–1058.

Kalinski et al., "Molecular Cloning of a Protein Associated with Soybean Seed Oil Bodies that is Similar to Thiol Proteases of the Papain Family" J. Biol. Chem. (1990) 265:13843–13848.

Bosch et al., "A trout growth hormone is expressed, correctly folded and partially glycosylated in the leaves but not the seeds of transgenic plants" Transgenic Research (1994) 3:304–310.

* cited by examiner

FIGURE 3A

```
1   ATG GCG GAT ACA GCT AGA GGA ACC CAT CAC GAT ATC ATC GGC AGA GAC CAG TAC CCG ATG  60
1    M   A   D   T   A   R   G   T   H   H   D   I   I   G   R   D   Q   Y   P   M   20

61  ATG GGC CGA GAC CGA GAC CAG TAC CAG ATG TCC GGA CGA GGA TCT GAC TAC TCC AAG TCT 120
21   M   G   R   D   R   D   Q   Y   Q   M   S   G   R   G   S   D   Y   S   K   S   40

121 AGG CAG ATT GCT AAA GCT GCA ACT GCT GTC ACA GCT GGT GGT TCC CTC CTT GTT CTC TCC 180
41   R   Q   I   A   K   A   A   T   A   V   T   A   G   G   S   L   L   V   L   S   60

181 AGC CTT ACC CTT GTT GGA ACT GTC ATA GCT TTG ACT GTT GCA ACA CCT CTG CTC GTT ATC 240
61   S   L   T   L   V   G   T   V   I   A   L   T   V   A   T   P   L   L   V   I   80

241 TTC AGC CCA ATC CTT GTC CCG GCT CTC ATC ACA GTT GCA CTC CTC ATC ACC GGT TTT CTT 300
81   F   S   P   I   L   V   P   A   L   I   T   V   A   L   L   I   T   G   F   L  100

301 TCC TCT GGA GGG TTT GGC ATT GCC GCT ATA ACC GTT TTC TCT TGG ATT TAC AAG TAC GCA 360
101  S   S   G   G   F   G   I   A   A   I   T   V   F   S   W   I   Y   K   Y   A  120

361 ACG GGA GAG CAC CCA CAG GGA TCA GAC AAG TTG GAC AGT GCA AGG ATG AAG TTG GGA AGC 420
121  T   G   E   H   P   Q   G   S   D   K   L   D   S   A   R   M   K   L   G   S  140

421 AAA GCT CAG GAT CTG AAA GAC AGA GCT CAG TAC TAC GGA CAG CAA CAT ACT GGT GGG GAA 480
141  K   A   Q   D   L   K   D   R   A   Q   Y   Y   G   Q   Q   H   T   G   G   E  160

481 CAT GAC CGT GAC CGT ACT CGT GGT GGC CAG CAC ACT ACT CTC GTT CCA CGA GGA TCC GAC 540
161  H   D   R   D   R   T   R   G   G   Q   H   T   T   L̲   V̲   P̲   R̲   G̲   S̲   D  180

541 AAC CAG CGG CTC TTC AAT AAT GCA GTC ATT CGT GTA CAA CAC CTG CAC CAG CTG GCT GCA 600
181  N   Q   R   L   F   N   N   A   V   I   R   V   Q   H   L   H   Q   L   A   A  200

601 AAA ATG ATT AAC GAC TTT GAG GAC AGC CTG TTG CCT GAG GAA CGC AGA CAG CTG AGT AAA 660
201  K   M   I   N   D   F   E   D   S   L   L   P   E   E   R   R   Q   L   S   K  220

661 ATC TTC CCT CTG TCT TTC TGC AAT TCT GAC TAC ATT GAG GCG CCT GCT GGA AAA GAT GAA 720
221  I   F   P   L   S   F   C   N   S   D   Y   I   E   A   P   A   G   K   D   E  240
```

FIGURE 3B

```
 721 ACA CAG AAG AGC TCT ATG CTG AAG CTT CTT CGC ATC TCT TTT CAC CTC ATT GAG TCC TGG 780
 241 T   Q   K   S   S   M   L   K   L   L   R   I   S   F   H   L   I   E   S   W   260

781 GAG TTC CCA AGC CAG TCC CTG AGC GGA ACC GTC TCA AAC AGC CTG ACC GTA GGG AAC CCC 840
 261 E   F   P   S   Q   S   L   S   G   T   V   S   N   S   L   T   V   G   N   P   280

841 AAC CAG CTC ACT GAG AAG CTG GCC GAC TTG AAA ATG GGC ATC AGT GTG CTC ATC CAG GCA 900
 281 N   Q   L   T   E   K   L   A   D   L   K   M   G   I   S   V   L   I   Q   A   300

901 TGT CTC GAT GGT CAA CCA AAC ATG GAT GAT AAC GAC TCC TTG CCG CTG CCT TTT GAG GAC 960
 301 C   L   D   G   Q   P   N   M   D   D   N   D   S   L   P   L   P   F   E   D   320

961 TTC TAC TTG ACC ATG GGG GAG AAC AAC CTC AGA GAG AGC TTT CGT CTG CTG GCT TGC TTC 1020
 321 F   Y   L   T   M   G   E   N   N   L   R   E   S   F   R   L   L   A   C   F   340

1021 AAG AAG GAC ATG CAC AAA GTC GAG ACC TAC TTG AGG GTT GCA AAT TGC AGG AGA TCC CTG 1080
 341 K   K   D   M   H   K   V   E   T   Y   L   R   V   A   N   C   R   R   S   L   360

1081 GAT TCC AAC TGC ACC CTG TAG
 361 D   S   N   C   T   L   *
```

EXPRESSION OF SOMATOTROPIN IN PLANT SEEDS

CROSS REFERENCE TO RELATED APPLICATIONS

The present application is a continuation-in-part of U.S. Ser. No. 08/846,021 that was filed on Apr. 25, 1997, now U.S. Pat. No. 5,948,682, which is a continuation-in-part of U.S. Ser. No. 08/366,783 that was filed on Dec. 30, 1994, now U.S. Pat. No. 5,650,554, which is a continuation-in-part of U.S. Ser. No. 08/142,418 that was filed Nov. 16, 1993, now abandoned, which is a continuation-in-part of U.S. Ser. No. 07/659,835 that was filed on Feb. 22, 1991, now abandoned, all of which are incorporated herein by reference.

FIELD OF THE INVENTION

The present invention provides novel transgenic plant seeds comprising a somatotropin as well as methods of preparing plant seeds comprising somatotropins.

BACKGROUND OF THE INVENTION

Naturally occurring somatotropins are polypeptides, the amino acid sequences of which for a number of vertebrate species have been reported. These include bovine (Miller et al., 1980, J. Biol. Chem, 255, 7251) porcine (Seeburg et al., 1983, DNA 2: 37), human (U.S. Pat. No. 3,853,832; Martial et al., Science, 205: 602–617) and various piscine somatotropins (e.g.: Sekine et al., 1985. Proc. Natl. Acad. Sci. (USA), 82: 4306–4310; Agellon et al., 1988, Proc. Natl. Acad. Sci. (USA), 85: 5136–5140; U.S. Pat. Nos. 4,689,402 and 4,894,362). In general, somatotropins isolated from different species display a high degree of amino acid sequence identity (Chang et al., 1992, Gen. and Comp. Endocrin. 87: 385–393). Analogs of somatotropins are also known. European Patent Application 103 395, for example discloses bovine somatotropin analogs. These analogs typically relate to the insertion, addition or deletion of nucleotides of the somatotropin gene thereby creating a protein different from the naturally occurring somatotropin.

The preparation of somatotropins is well known in the art. Bovine somatotropin, for example can be prepared by extraction from the pituitary tissue, (Li et al., 1954, J. Biol. Chem. 211: 55 and U.S. Pat. No. 4,371,462). Somatotropins can also be prepared by production in genetically engineered microorganisms, such as *Escherichia coli* containing recombinant DNA which encodes a somatotropin polypeptide (e.g. Seeburg et al., 1978, Nature). U.S. Pat. No. 4,443,549 discloses a method for producing bovine somatotropin in yeast cells. Methods for high yield bovine somatotropin production in microorganisms are disclosed in U.S. Pat. Nos. 5,240,837 and 5,489,529.

Similarly, the preparation of human somatotropin is known. For example U.S. Pat. No. 5,637,495 and Mukhija et al. (Gene 165: 303–306) teach the production of human growth hormone in *E. coli*.

Fish somatotropins have also been produced in a variety of microorganisms. U.S. Pat. No. 5,270,180 for example discloses a method for the production of salmon growth hormone in *E. coli* and yeast and in U.S. Pat. No. 4,894,362 a microbial production system for eel growth hormone is disclosed.

The low costs associated with growing plants, make plants an attractive host for the production of somatotropins. To the best of the present inventors knowledge only one attempt has been reported to produce a somatotropin in plants. Bosch et al. (Transgenic Research, 1994, 3: 304–310) expressed a trout growth hormone in the leaves of transgenic tobacco plants, however they were unsuccessful in accumulating somatotropin in seeds.

Although methods for producing somatotropins are well known to skilled artisans, the existing methods are relatively expensive, especially when large production volumes are required. Accordingly there is a need in the art for additional economical production methods of somatotropin.

SUMMARY OF THE INVENTION

The present inventors have discovered a cost effective method for the preparation of somatotropins in the seeds of plants. The method involves expressing a somatotropin in plant seeds as an oleosin fusion protein so that the somatotropin has biological activity.

Accordingly, the present invention provides a method for the expression of a somatotropin in a plant comprising:

(a) introducing into a plant cell a chimeric nucleic acid sequence comprising:
  (1) a first nucleic acid sequence capable of regulating the transcription in said host cell of
  (2) a second nucleic acid sequence, wherein said second sequence encodes a recombinant fusion polypeptide and comprises (i) a nucleic acid sequence encoding a sufficient portion of an oleosin protein to provide targeting of the recombinant fusion polypeptide to a lipid phase, linked in frame to (ii) a nucleic acid sequence encoding said somatotropin; and
  (3) a third nucleic acid sequence encoding a termination region functional in said plant cell; and (b) growing said plant cell to produce said recombinant fusion polypeptide.

In a preferred embodiment of the invention, the somatotropin is fish growth hormone. In a further preferred embodiment of the invention the somatotropin is carp growth hormone.

In another aspect the invention provides a chimeric nucleic acid sequence, capable of being expressed in association with an oil body of a plant cell, comprising:

(1) a first nucleic acid sequence capable of regulating the transcription in said plant cell (2) a second nucleic acid sequence, wherein said second sequence encodes a recombinant fusion polypeptide and comprises (i) a nucleic acid sequence encoding a sufficient portion of an oleosin protein to provide targeting of the recombinant fusion polypeptide to a lipid phase, linked in reading frame to (ii) a nucleic acid sequence encoding a somatotropin; and (3) a third nucleic acid sequence encoding a termination region functional in said host cell.

In a further aspect, the instant invention provides plant seeds expressing a somatotropin. In one embodiment of the invention the somatotropin is a fish growth hormone.

BRIEF DESCRIPTION OF THE DRAWINGS

The invention will now be described in relation to the drawings in which:

FIG. 3A is a part of nucleic acid sequence (SEQ.ID.NO.:1) and deduced amino acid sequence (SEQ.ID.NO.:2) of the olesin-cGH fusion sequence.

FIG. 3B is a continuation of the nucleic acid sequence (SED.ID.NO.:1) and deduced amino acid sequence (SEQ.ID.NO.:2) of the olesin-cGH fusion dequence.

DETAILED DESCRIPTION OF THE INVENTION

Figure 1:
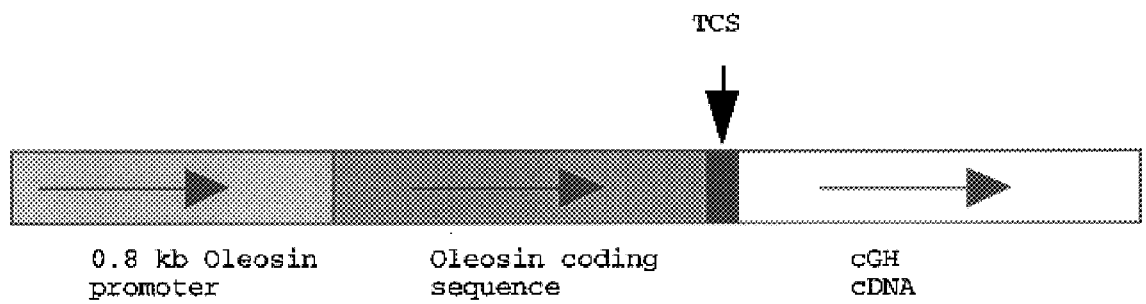
FIG. 1 is a schematic diagram of the oleosin-cGH fusion construct.

The present invention relates to the production of somatotropins. Somatotropins, frequently referred to in the art as growth hormones, are anabolic hormones produced by the vertebrate pituitary gland. In general, somatotropins display pleiotropic biological effects, which include promotion of skeletal growth and stimulation of mammalian milk secretion. Accordingly it has been recognized that the use of somatotropins results in improvements of the production economics in industries such as aquaculture and the livestock industry.

As hereinbefore mentioned, the present invention provides transgenic plant seeds comprising a somatotropin as well as methods of preparing plant seeds comprising somatotropins.

Accordingly the present invention provides a method for the expression of a somatotropin in a plant cell comprising:
 (a) introducing into a plant cell a chimeric nucleic acid sequence comprising:
  (1) a first nucleic acid sequence capable of regulating the transcription in said plant cell of
  (2) a second nucleic acid sequence, wherein said second nucleic acid sequence encodes a recombinant fusion polypeptide and comprises (i) a nucleic sequence encoding a sufficient portion of an oleosin protein to provide targeting of the recombinant fusion polypeptide to a lipid phase, linked in frame to (ii) a nucleic sequence encoding a somatotropin; and
  (3) a third nucleic acid sequence encoding a termination region functional in said plant cell; and
 (b) growing said plant cell to produce said recombinant fusion polypeptide.

The term "somatotropin" as used herein comprises any active somatotropin, including bovine, ovine, avian, canine, piscine, porcine, rat and human somatotropin or any biologically active analogs or fragments thereof, including somatotropin derivatives which have been obtained by, adding, deleting or substituting amino acids or by otherwise modifying the structure of any naturally occurring somatotropin. Throughout this application the term "somatotropin" is used interchangeably with the term "growth hormone".

The term "nucleic acid sequence" refers to a sequence of nucleotide or nucleoside monomers consisting of naturally occurring bases, sugars and intersugar (backbone) linkages. The term also includes modified or substituted sequence comprising non-naturally occurring monomers or portions thereof, which function similarly. The nucleic acid sequences of the present invention may be ribonucleic (RNA) or deoxyribonucleic acids (DNA) and may contain naturally occurring bases adenine, guanine, cytosine, thymidine and uracil. The sequences may also contain modified bases such as xanthine, hypoxanthine, 2-aminoadenine, 6-methyl, 2 propyl and other alkyl adenines, 5 halo uracil, 5 halo cytosine, 6-aza uracil, 6-aza cytosine, abd 6-aza thymine, pseudo uracil, 4-thioruacil, 8-halo adenine, 8-amino adenine, 8-thiol adenine, 8-thiolalkyl adenines, 8-hydroxyl, adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-thrifluoromethyl uracil and 5-trifluoro cytosine.

The term "sufficient portion of an oleosin protein to provide targeting of the recombinant fusion polypeptide to a lipid phase" means any oleosin protein or any analog or portion thereof, including oleosin derivatives which have been obtained by, adding, deleting or substituting amino acids or by otherwise modifying the structure of any naturally occurring oleosin which is capable of targeting to a lipid phase. Lipid phase is intended to mean any subcellular structure comprising triacylglycerides, including oil bodies and other organelles comprising membranes or membrane like structures such as the endoplasmatic reticulum or the chloroplast.

The nucleic acid and amino acid sequences of numerous somatotropins including, bovine (Miller et al., 1980, J. Biol. Chem, 255, 7251) porcine (Seeburg et al., 1983, DNA 2: 37), human (U.S. Pat. No. 3,853,832; Martial et al., Science, 205: 602–617) and various piscine somatotropins (e.g.: Sekine et al., 1985. Proc. Natl. Acad. Sci. (USA), 82: 4306–4310; Agellon et al., 1988, Proc. Natl. Acad. Sci. (USA), 85: 5136–5140; U.S. Pat. Nos. 4,689,402 and 4,894,362) are available. Analogs of somatotropins are also known (e.g. European Patent Application 103 395). In preferred embodiments of the present invention the somatotropin is a fish somatotropin. In a particularly preferred embodiment of the invention the somatotropin is a carp somatotropin. Based on the sequences cDNA clones comprising the genetic material encoding the somatotropins may be prepared and oleosin fusion genes may be prepared in accordance with the present invention and practicing techniques commonly known to those skilled in the art (see e.g. Sambrook et al. (1990), Molecular Cloning, 2nd ed., Cold Spring Harbor Press).

To identify other somatotropins having desired characteristics, a nucleic acid probe may be designed and prepared to identify additional somatotropins. The nucleic acid probe may be used to screen cDNA or genomic libraries from any living cell or virus. Sequences which hybridize with the probe under stringent conditions may then be isolated. Given the sequence identity of the somatotropins isolated from different species to date (Chang et al., 1992, Gen. and Comp. Endocrin. 87: 385–393) somatotropins from a broad range of species may be isolated according to this method.

Somatotropin sequences may also be isolated by screening expression libraries. Antibodies against existing somatotropins may be obtained and expression libraries may be screened with these antibodies essentially as described by Huynh et al. (1985, in DNA cloning, Vol 1, a Practical Approach ed. D. M. Glover, IRL Press). Expression libraries may be prepared from any living cell or virus.

Other somatotropins may be discovered by those skilled in the art. The actual somatotropin sequence which is selected is not of critical importance and may be as desired. It is to be clearly understood that any somatotropin may be employed without departing from the spirit or scope of the present invention.

The chimeric nucleic acid sequences which encode the oleosin-somatotropin fusion proteins of the present invention can be incorporated in a known manner into a recombinant expression system which ensures expression in the plant host cell. Accordingly, the present invention also includes a recombinant expression vector comprising a chimeric nucleic acid sequence operatively linked to a regulatory sequence and termination region suitable for expression in a host cell. In one embodiment the invention provides a chimeric nucleic acid sequence, capable of being expressed in association with an oil body of a plant cell, comprising:

(1) a first nucleic acid sequence capable of regulating the transcription in said plant cell (2) a second nucleic acid sequence, wherein said second sequence encodes a recombinant fusion polypeptide and comprises (i) a nucleic acid sequence encoding a sufficient portion of an oleosin protein to provide targeting of the recombinant fusion polypeptide to a lipid phase, linked in reading frame to (ii) a nucleic acid sequence encoding a somatotropin; and (3) a third nucleic acid sequence encoding a termination region functional in said host cell.

The nucleic acid sequence encoding the somatotropin may be genetically fused upstream or downstream of the nucleic acid sequence encoding the oleosin protein and concatamers containing repetitive units of the somatotropin may be employed. In preferred embodiments, the somatotropin gene is fused downstream of the oleosin gene.

The present invention provides plant seeds which recombinantly express somatotropins. In a preferred embodiment of the present these seeds are obtained from a dicotelydenous plant. In a yet further preferred embodiment the seeds are exalbuminous seeds. In a further preferred embodiment of the instant invention the plant seeds are obtained from the group of plant species comprising: rapeseed (Brassica spp.), linseed/flax (*Linum usitatissimum*), safflower (*Carthamus tinctorius*), sunflower (*Helianthus annuus*), maize (*Zea mays*), soybean (*Glycine max*), mustard (Brassica spp. and *Sinapis alba*), crambe, (*Crambe abyssinica*), eruca (*Eruca sativa*), oil palm (*Elaeis guineeis*), cottonseed (Gossypium spp.), groundnut (*Arachis hypogaea*), coconut (*Cocus nucifera*), castor bean (*Ricinus communis*), coriander (*Coriandrum sativum*), squash, (*Cucurbita maxima*), Brazil nut (*Bertholletia excelsa*) and jojoba (*Simmondsia chinensis*). It is expected that the somatotropin is expressed in all embryonic tissue, although difference in expression levels may be detected in different tissues of the embryonic axis and the cotyledon.

(I) CLONING, PLANT TRANSFORMATION AND REGENERATION

Cloning and Transformation Vectors

Two types of vectors are routinely employed. The first type of vector is used for the genetic-engineering and assembly of constructs and typically consists of a backbone such as found in the pUC family of vectors, enabling replication in easily-manipulated and maintained gram negative bacteria such as *E. coli*. The second type of vector typified by the Ti and Ri plasmids, specify DNA transfer functions and are used when it is desired that the constructs be introduced into the plant and stably integrated into its genome via Agrobacterium-mediated transformation.

A typical construct consists, in the 5' to 3' direction, of a regulatory region complete with a promoter capable of directing expression in plants (preferably seed-specific expression), a protein coding region, and a sequence containing a transcriptional termination signal functional in plants. The sequences comprising the construct may be either natural or synthetic or any combination thereof.

Both non-seed specific promoters, such as the 35-S CaMV promoter (Rothstein et al., 1987; Gene 53: 153–161) and seed-specific promoters such as the phaseolin promoter (Sengupta-Gopalan et al., 1985; PNAS USA 82: 3320–3324) or the Arabidopsis 18 kDa oleosin (Van Rooijen et al., 1992; Plant Mol. Biol. 18: 1177–1179) promoters may be used. In addition to the promoter, the regulatory region contains a ribosome binding site enabling translation of the transcripts in plants and may also contain one or more enhancer sequences, such as the AMV leader (Jobling and Gehrke 1987; Nature 325: 622–625), to increase the expression of product.

The coding region of the construct will typically be comprised of sequences encoding a ligand fused in frame to an oleosin and ending with a translational termination codon. The sequence for the oleosin may be comprised of any DNA sequence, or part thereof, natural or synthetic, sufficient to encode a protein that can be correctly targeted to, and stably expressed on, an oil body. A detailed description of the characteristics of such a sequence has been reported previously in Moloney, 1993; PCT Patent Appl. WO 93/21320 which is hereby incorporated by reference. The sequence may also include introns. The ligand-encoding region may in turn be comprised of any individual, or combination of, ligand sequences identified as described above. If desired, a protease or chemical recognition site may be engineered between the ligand and the target protein to enable proteolytic removal of the ligand from the target protein in the course of purification.

The region containing the transcriptional termination signal may comprise any such sequence functional in plants such as the nopaline synthase termination sequence and additionally may include enhancer sequences to increase the expression of product.

The various components of the construct are ligated together using conventional methods, typically into a pUC-based vector. This construct may then be introduced into an Agrobacterium vector and subsequently into host plants, using one of the transformation procedures outlined below.

Transformation of Plants

A variety of techniques is available for the introduction of DNA into host cells. For example, the chimeric DNA constructs may be introduced into host cells obtained from dicotyledonous plants, such as tobacco, and oleaginous species, such as *B. napus* using standard Agrobacterium vectors; by a transformation protocol such as that described by Moloney et al., 1989, (Plant Cell Rep., 8: 238–242) or Hinchee et al., 1988, (Bio/Technol., 6: 915–922); or other techniques known to those skilled in the art. For example, the use of T-DNA for transformation of plant cells has received extensive study and is amply described in EPA Ser. No. 120,516; Hoekema et al., 1985, (Chapter V, In: The Binary Plant Vector System Offset-drukkerij Kanters B. V., Alblasserdam); Knauf, et al., 1983, (Genetic Analysis of Host Range Expression by Agrobacterium, p. 245, In Molecular Genetics of the Bacteria-Plant Interaction, Puhler, A. ed., Springer-Verlag, N.Y.); and An et al., 1985, (EMBO J., 4: 277–284). Conveniently, explants may be cultivated with *A. tumefaciens* or *A. rhizogenes* to allow for transfer of the transcription construct to the plant cells. Following transformation using Agrobacterium the plant cells are dispersed in an appropriate medium for selection, subsequently callus, shoots and eventually plantlets are recovered. The Agrobacterium host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non-Agrobacterium techniques permits the use of the constructs described herein to obtain transformation and expression in a wide variety of monocotyledonous and dicotyledonous plants and other organisms. These techniques are especially useful for species that are intractable in an Agrobacterium transformation system. Other techniques for gene transfer include biolistics (Sanford, 1988, Trends in Biotech., 6: 299–302), electroporation (Fromm et al., 1985, Proc. Natl. Acad. Sci. USA, 82: 5824–5828; Riggs and Bates, 1986, Proc. Natl. Acad. Sci. USA 83: 5602–5606) or PEG-mediated DNA uptake (Potrykus et al., 1985, Mol. Gen. Genet., 199: 169–177).

In a specific application, such as to *B. napus*, the host cells targeted to receive recombinant DNA constructs typically will be derived from cotyledonary petioles as described by Moloney et al., (1989, Plant Cell Rep., 8: 238–242). Other examples using commercial oil seeds include cotyledon transformation in soybean explants (Hinchee et al., 1988. Bio/Technology, 6: 915–922) and stem transformation of cotton (Umbeck et al., 1981, Bio/Technology, 5: 263–266). Regeneration and Analysis of Transgenic Plants Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic DNA using an appropriate probe, for example an *A. thaliana* oleosin gene, to show that integration of the desired sequences into the host cell genome has occurred.

The expression cassette will normally be joined to a marker for selection in plant cells. Conveniently, the marker may be resistance to a herbicide, e.g. phosphinothricin or glyphosate, or more particularly an antibiotic, such as kanamycin, G418, bleomycin, hygromycin, chloramphenicol, or the like. The particular marker employed will be one which will allow for selection of transformed cells compared with cells lacking the introduced recombinant DNA.

The fusion peptide in the expression cassette constructed as described above, expresses at least preferentially in developing seeds. Accordingly, transformed plants grown in accordance with conventional ways, are allowed to set seed. See, for example, McCormick et al. (1986, Plant Cell Reports, 5: 81–84). Northern blotting can be carried out using an appropriate gene probe with RNA isolated from tissue in which transcription is expected to occur, such as a seed embryo. The size of the transcripts can then be compared with the predicted size for the fusion protein transcript.

Oil body proteins are then isolated from the seed and analyses performed to determine that the fusion peptide has been expressed. Analyses can be for example by SDS-PAGE. The fusion peptide can be detected using an antibody to the oleosin portion of the fusion peptide. The size of the fusion peptide obtained can then be compared with predicted size of the fusion protein.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well know to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, (e.g.: treatment with colchicine or other microtubule disrupting agents).

(II) RECOVERY OF THE POLYPEPTIDE

The present invention also includes a fusion polypeptides encoded for by a chimeric nucleic acid sequence comprising (i) a nucleic acid sequence encoding a sufficient portion of an oil body protein to provide targeting of the fusion polypeptide to an oil body linked in reading frame to (ii) a nucleic acid sequence encoding a somatotropin. Preferably the fusion polypeptide displays growth hormone activity. Consequently, the present invention includes a fusion polypeptide comprising a somatotropin wherein the expressed somatotropin moiety is biologically active. In preferred embodiments of the invention, the fusion polypeptide comprises an oleosin protein fused to a somatotropin, wherein the chimeric protein displays growth hormone activity.

The invention further provides methods for the separation of the fusion protein from host cell components by partitioning of the oil body fraction. Optionally, the recombinant somatotropin may be released from the fusion protein via specific cleavage of the somatotropin—oil body protein fusion. Optionally a cleavage site may be located prior to the N-terminus and after the C-terminus of the somatotropin allowing the fusion polypeptide to be cleaved and separated by phase separation into its component peptides.

In preferred embodiments of the present invention, seeds are crushed upon harvesting by grinding, pulverizing or otherwise breaking open the seed cells using milling equipment, for example flaking rolls, disk mills, colloid mils, pin mills, orbital mills IKA mills or industrial style homogenizers. In one embodiment of the present invention, the crushed seed fraction may directly be employed as an ingredient to formulate compositions, such as animal feed compositions, comprising somatotropin. In alternative embodiments of the invention a seed fraction comprising somatotropin is isolated. In a preferred embodiment of the present invention, the isolated seed fraction comprises intact oil bodies. In order to isolate the oil body fraction of the seeds, plant seeds are preferably first crushed. In one embodiment the crushed seed fraction is subsequently submitted to density centrifugation resulting in a separation of the oil body fraction from the aqueous seed fraction. Density centrifugation may be accomplished using decantation centrifuges, including 2-phase and 3-phase decanters, hydrocyclones or disc stack centrifuges. It is also possible to separate the oil body fraction from the aqueous fraction employing size exclusion methods such as membrane ultrafiltration and crossflow microfiltration. The oil bodies may be washed one or more times using preferably water, buffered solutions or other aqueous solutions in order to remove undesirable seed components.

In a further preferred embodiment the somatotropin polypeptide is purified from the seed cells. This is particularly advantageously done by first isolating the oil body fraction as hereinbefore described and subsequently separating the somatotropin polypeptide from the oil body fraction. If a linker comprising a protease cleavage site has been included in the expression cassette, a protease specific for the recognition motif may be added to the oil body preparation. This results in the release of the somatotropin from the oil body. A centrifugation step will result in partitioning of the somatotropin into the aqueous phase. Subsequent purification steps known to the skilled biochemist may be applied to the aqueous fraction in order to obtain a further degree of purity if so desired.

The following non-limiting examples are illustrative of the present invention:

EXAMPLES

Example 1
Expression of Somatotropin in *Brassica napus*

In this example, the expression of carp growth hormone in canola seed is described as well as the purification oil bodies comprising carp growth hormone.

Construction of Oleosin-cGH Gene Fusion

The fragment of the cGH cDNA (Koren et al., Nucl. Acids Res. 10: 2177–2187) encoding the full length functional protein was modified by site-directed mutagenesis to contain a BamHI and a KpnI site at its 5' and 3' ends respectively, and cloned in pUC19 to generate pUCGH. The *Arabidopsis thaliana* 18 kDa oleosin gene containing 800 base pairs of its promoter was previously isolated in our laboratory (U.S. Pat. No. 5,792,922) and engineered to contain sequences encoding a thrombin cleavage site at the 3' end of the oleosin coding region, followed by a BamHI restriction endonuclease site. This gene was cloned in pUC19 and designated pOthromb (Van Rooijen, 1993, PhD Thesis, University of Calgary). The cGH cDNA was fused to the 3' end of the oleosin gene using the BamHI site. The fusion construct is shown in FIGS. 1 and 3.

FIG. 1 is a schematic diagram of the oleosin-cGH fusion construct. The oleosin coding sequence, the oleosin promoter sequence and the carp growth hormone cDNA sequence are indicated. A thrombin cleavage site (TCS) is indicated with an arrow. FIG. 3 shows the nucleic acid sequence and deduced amino acid sequence of the oleosin-cGH fusion sequence. The deduced amino acid sequence of cGH has been italicized. A thrombin cleavage site has been underlined.

The cassette was subsequently inserted in the multiple cloning site of a plant transformation vector generating the pCGoleoGH800 plasmid.

Plant Transformation

The construct pCGOleoGH800 was electroporated into *Agrobacterium tumefaciens* (Dower et al., 1988, Nucl. Acids Res. 16: 6127–6145). A single positive colony was selected and used to transform *B. napus* (cv Westar) cotyledonary explants using the Agrobacterium-mediated transformation method described by Moloney et al., 1989, Plant Cell Reports 8: 238–242 followed by plant regeneration.

Oil Body Preparation

Seeds were harvested, crushed and homogenized in five volumes of buffer A (100 mM Tris, 500 mM NaCl, 10 mM EDTA, pH 8.0) using a Polytron, and centrifuged at 10,000×g for 10 minutes. Oil bodies were skimmed from the surface of the supernatant with a metal spatula, re-suspended in buffer and re-centrifuged. Two washes were performed using buffer A, followed by two washes using buffer B (20 mM sodium phosphate, pH 7.3 or PBS as required). Oil bodies were subsequently suspended in buffer B and stored on ice.

Protein Analysis

To extract oil body proteins, oil bodies were boiled in the extraction buffer for 10 minutes. Insoluble material was than removed by centrifugation. Soluble proteins were quantified using the BCA Protein assay (Pierce), and analyzed by 12% SDS-PAGE followed by Western blotting. An anti-cGH rabbit antiserum was used as the primary antibody, and A goat anti-rabbit-IgG [H+L]-AP conjugate (Bio-Rad) was used as the secondary antibody.

Figure 2:
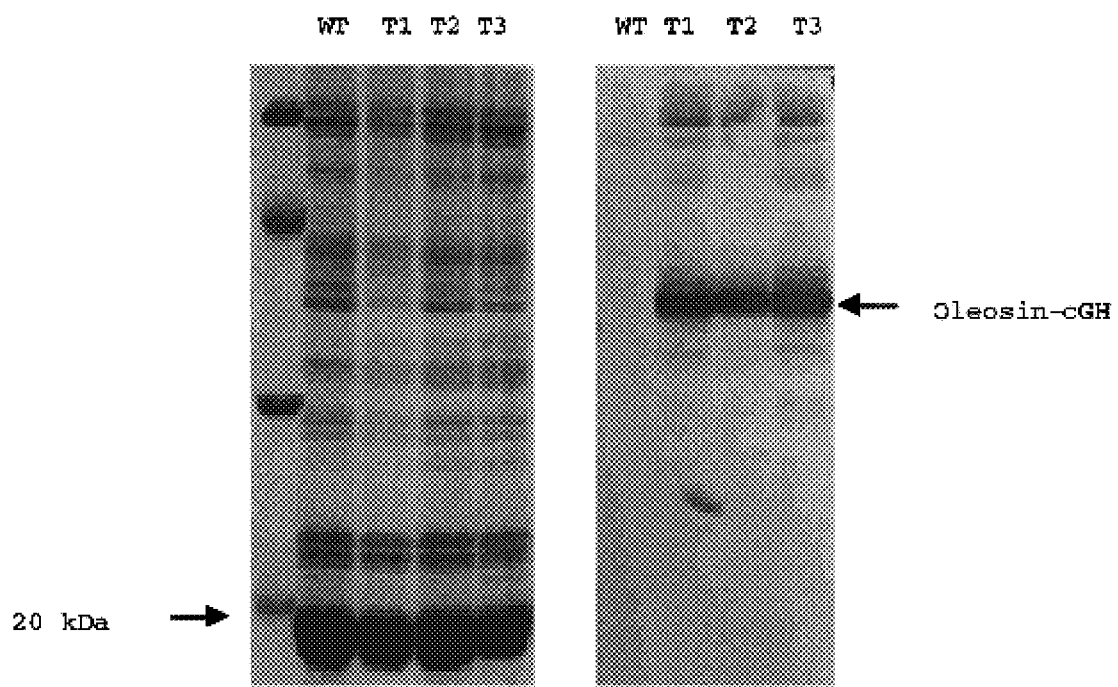
FIG. 2 shows The expression of oleosin-carp growth hormone fusion in protein in three generations of canola seed.

The expression of the oleosin-carp growth hormone fusion in three generations of canola seed is shown in FIG. 2. FIG. 2 shows the SDS-PAGE (Left) and Western Blot (Right) analysis of oil body proteins from seeds of a wild-type (WT) and first (T1), second (T2) and third (T3) generation of plants expressing an oleosin c-GH fusion protein. M; low molecular mass protein markers. A total of 30 μg of protein was loaded into each lane.

We claim:

1. A method for the expression of a somatotropin in plants said method comprising:
   (a) introducing into a plant cell a chimeric nucleic acid sequence comprising:
      (1) a first nucleic acid sequence capable of regulating the transcription in said host cell of
      (2) a second nucleic acid sequence, wherein said second sequence encodes a recombinant fusion polypeptide and comprises (i) a nucleic acid sequence encoding a sufficient portion of an oleosin protein to provide targeting of the recombinant fusion polypeptide to a lipid phase, linked in frame to (ii) a nucleic acid sequence encoding said somatotropin; and
      (3) a third DNA sequence encoding a termination region functional in said plant cell; and
   (b) growing said plant cell to produce said recombinant fusion polypeptide.

2. The method according to claim 1 further including separating the recombinant fusion polypeptide from cellular host cell components by selective partitioning into a lipid phase.

3. The method according to claim 1 further including separating the recombinant fusion polypeptide from cellular host components by selective partitioning into a lipid phase comprising oil bodies.

4. The method according to claim 3 wherein said recombinant fusion polypeptide is separated by addition of oil body components and reconstitution of the oil bodies.

5. A method according to claim 1 wherein said somatotropin is a fish growth hormone.

6. A method according to claim 5 wherein said fish growth hormone is carp growth hormone.

7. A chimeric nucleic acid sequence encoding a recombinant fusion polypeptide comprising (i) a nucleic acid sequence encoding a sufficient portion of an oleosin protein to provide targeting of the recombinant fusion polypeptide to a lipid phase, linked in reading frame to (ii) a nucleic acid sequence encoding a somatotropin.

8. A chimeric nucleic acid sequence according to claim 7 having the nucleic acid sequence shown in SEQ.ID.NO.:1.

9. A chimeric nucleic acid sequence, capable of being expressed in association with an oil body of a plant cell, comprising:
   (1) a first nucleic acid sequence capable of regulating the transcription in said plant cell
   (2) a second nucleic acid sequence, wherein said second sequence encodes a recombinant fusion polypeptide and comprises (i) a nucleic acid sequence encoding a sufficient portion of an oleosin protein to provide targeting of the recombinant fusion polypeptide to a lipid phase, linked in reading frame to (ii) a nucleic acid sequence encoding a somatotropin; and
   (3) a third nucleic acid sequence encoding a termination region functional in said host cell.

10. A chimeric nucleic acid sequence according to claim 9 wherein said somatotropin is a fish growth hormone.

11. A chimeric nucleic acid sequence according to claim 10 wherein said fish growth hormone is carp growth hormone.

12. A plant transformed with a chimeric nucleic acid sequence according to claim 9.

13. A plant according to claim 10 wherein said plant is selected from the group consisting of rapeseed (Brassica spp.), linseed/flax (*Linum usitatissimum*), safflower (*Carthamus tinctorius*), sunflower (*Helianthus annuus*), maize (*Zea mays*), soybean (*Glycine max*), mustard (Brassica spp. and *Sinapis alba*), crambe, (*Crambe abyssinica*), eruca (*Eruca sativa*), oil palm (*Elaeis guineeis*), cottonseed (Gossypium spp.), groundnut (*Arachis hypogaea*), coconut (*Cocus nucifera*), castor bean (*Ricinus communis*), coriander (*Coriandrum sativum*), squash, (*Cucurbita maxima*), Brazil nut (*Bertholletia excelsa*) and jojoba (*Simmondsia chinensis*).

14. A plant seed containing a chimeric nucleic acid sequence according to claim 9.

15. A plant seed according to claim 14 wherein said seed is obtained from a dicotelydenous plant.

16. A plant seed according to claim 14 wherein said somatotropin is expressed in the embryogenic tissue of the seed.

17. A plant seed comprising a recombinantly expressed somatotropin as a fusion protein with an oleosin.

18. A plant seed according to claim 17 wherein said somatotropin is expressed in the embryogenic tissue of said seed.

19. A plant seed according to claim 18 wherein said somatotropin is fish growth hormone.

* * * * *

SEQUENCE LISTING

```
<160> NUMBER OF SEQ ID NOS: 2

<210> SEQ ID NO 1
<211> LENGTH: 1101
<212> TYPE: DNA
<213> ORGANISM: synthetic construct

<400> SEQUENCE: 1
atggcggata cagctagagg aacccatcac gatatcatcg gcagagacca gtacccgatg      60
atgggccgag accgagacca gtaccagatg tccggacgag gatctgacta ctccaagtct     120
aggcagattg ctaaagctgc aactgctgtc acagctggtg gttccctcct tgttctctcc     180
agccttaccc ttgttggaac tgtcatagct ttgactgttg caacacctct gctcgttatc     240
ttcagcccaa tccttgtccc ggctctcatc acagttgcac tcctcatcac cggttttctt     300
tcctctggag ggtttggcat tgccgctata accgtttttct cttggattta caagtacgca    360
acgggagagc acccacaggg atcagacaag ttggacagtg caaggatgaa gttgggaagc    420
aaagctcagg atctgaaaga cagagctcag tactacggac agcaacatac tggtggggaa    480
catgaccgtg accgtactcg tggtggccag cacactactc tcgttccacg aggatccgac    540
aaccagcggc tcttcaataa tgcagtcatt cgtgtacaac acctgcacca gctggctgca   600
```

-continued

```
aaaatgatta acgactttga ggacagcctg ttgcctgagg aacgcagaca gctgagtaaa       660
atcttccctc tgtctttctg caattctgac tacattgagg cgcctgctgg aaaagatgaa       720
acacagaaga gctctatgct gaagcttctt cgcatctctt ttcacctcat tgagtcctgg       780
gagttcccaa gccagtccct gagcggaacc gtctcaaaca gcctgaccgt agggaacccc       840
aaccagctca ctgagaagct ggccgacttg aaaatgggca tcagtgtgct catccaggca       900
tgtctcgatg gtcaaccaaa catggatgat aacgactcct tgccgctgcc ttttgaggac       960
ttctacttga ccatggggga gaacaacctc agagagagct tcgtctgct ggcttgcttc       1020 aagaaggaca tgcacaaagt cgagacctac ttgagggttg caaattgcag gagatccctg      1080
gattccaact gcaccctgta g                                                1101
```

```
<210> SEQ ID NO 2
<211> LENGTH: 366
<212> TYPE: PRT
<213> ORGANISM: synthetic construct

<400> SEQUENCE: 2
```

```
Met Ala Asp Thr Ala Arg Gly Thr His His Asp Ile Ile Gly Arg Asp
  1               5                  10                  15

Gln Tyr Pro Met Met Gly Arg Asp Arg Asp Gln Tyr Gln Met Ser Gly
                 20                  25                  30

Arg Gly Ser Asp Tyr Ser Lys Ser Arg Gln Ile Ala Lys Ala Ala Thr
             35                  40                  45

Ala Val Thr Ala Gly Gly Ser Leu Leu Val Leu Ser Ser Leu Thr Leu
         50                  55                  60

Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                 85                  90                  95

Thr Gly Phe Leu Ser Ser Gly Gly Phe Gly Ile Ala Ala Ile Thr Val
                100                 105                 110

Phe Ser Trp Ile Tyr Lys Tyr Ala Thr Gly Glu His Pro Gln Gly Ser
            115                 120                 125

Asp Lys Leu Asp Ser Ala Arg Met Lys Leu Gly Ser Lys Ala Gln Asp
        130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr Leu Val Pro
                165                 170                 175

Arg Gly Ser Asp Asn Gln Arg Leu Phe Asn Asn Ala Val Ile Arg Val
            180                 185                 190

Gln His Leu His Gln Leu Ala Ala Lys Met Ile Asn Asp Phe Glu Asp
        195                 200                 205

Ser Leu Leu Pro Glu Glu Arg Arg Gln Leu Ser Lys Ile Phe Pro Leu
    210                 215                 220

Ser Phe Cys Asn Ser Asp Tyr Ile Glu Ala Pro Ala Gly Lys Asp Glu
225                 230                 235                 240

Thr Gln Lys Ser Ser Met Leu Lys Leu Leu Arg Ile Ser Phe His Leu
                245                 250                 255

Ile Glu Ser Trp Glu Phe Pro Ser Gln Ser Leu Ser Gly Thr Val Ser
            260                 265                 270

Asn Ser Leu Thr Val Gly Asn Pro Asn Gln Leu Thr Glu Lys Leu Ala
        275                 280                 285
```

```
Asp Leu Lys Met Gly Ile Ser Val Leu Ile Gln Ala Cys Leu Asp Gly
    290                 295                 300

Gln Pro Asn Met Asp Asp Asn Asp Ser Leu Pro Leu Pro Phe Glu Asp
305                 310                 315                 320

Phe Tyr Leu Thr Met Gly Glu Asn Asn Leu Arg Glu Ser Phe Arg Leu
                325                 330                 335

Leu Ala Cys Phe Lys Lys Asp Met His Lys Val Glu Thr Tyr Leu Arg
                340                 345                 350

Val Ala Asn Cys Arg Arg Ser Leu Asp Ser Asn Cys Thr Leu
                355                 360                 365
```